(12) United States Patent
Tamez (10) Patent No.: US 9,047,750 B2
(45) Date of Patent: Jun. 2, 2015

(54) MOVEMENT MONITORING (71) Applicant: Cellco Partnership, Arlington, VA (US)

(72) Inventor: Dawn Tamez, Woodstock, GA (US)

(73) Assignee: Cellco Partnership, Basking Ridge, NJ (US)

( * ) Notice: Subject to any disclaimer, the term of this patent is extended or adjusted under 35 U.S.C. 154(b) by 139 days.

(21) Appl. No.: 13/788,386

(22) Filed: Mar. 7, 2013

(65) Prior Publication Data

US 2014/0253324 A1    Sep. 11, 2014

(51) Int. Cl.
*G08B 1/08* (2006.01)
*G08B 21/04* (2006.01)
*A61B 5/113* (2006.01)
*A61B 5/00* (2006.01)

(52) U.S. Cl.
CPC ........... *G08B 21/0461* (2013.01); *A61B 5/6892* (2013.01); *A61B 5/7405* (2013.01); *A61B 5/7455* (2013.01); *A61B 5/746* (2013.01); *A61B 5/747* (2013.01); *A61B 5/1135* (2013.01); *A61B 2562/0247* (2013.01); *A61B 2562/0252* (2013.01); *A61B 2562/0261* (2013.01)

(58) Field of Classification Search
None
See application file for complete search history.

(56) References Cited

U.S. PATENT DOCUMENTS

| | | | |
|---|---|---|---|
| 6,646,556 B1 * | 11/2003 | Smith et al. | 340/573.1 |
| 7,030,764 B2 * | 4/2006 | Smith et al. | 340/573.1 |
| 2001/0001235 A1 * | 5/2001 | Menkedick et al. | 340/573.1 |
| 2004/0046668 A1 * | 3/2004 | Smith et al. | 340/573.7 |
| 2007/0288263 A1 * | 12/2007 | Rodgers | 705/2 |
| 2008/0120784 A1 * | 5/2008 | Warner et al. | 5/658 |
| 2011/0144548 A1 * | 6/2011 | Elliott et al. | 601/49 |
| 2011/0190594 A1 * | 8/2011 | Heit et al. | 600/301 |
| 2012/0154582 A1 * | 6/2012 | Johnson et al. | 348/143 |

* cited by examiner

*Primary Examiner* — Travis Hunnings (57) ABSTRACT

A monitoring device includes a memory with a management application installed thereon. The application is configured to process a sensor signal generated by a sensor system configured between a patient and a corresponding surface, the sensor signal being configured based on a physiological movement detected by the sensor system, analyze the sensor signal utilizing a monitoring heuristic associated with a patient profile. The monitoring heuristic is configured to identify physiological movement patterns over time within the sensor signal and generate an output based on the physiological movement patterns.

24 Claims, 4 Drawing Sheets

Figure 4

MOVEMENT MONITORING

BACKGROUND

Hospitals and other medical facilities utilize advanced life support systems to prevent the loss of a patient (e.g., person or animal under medical care and treatment). Advanced life support systems generally require the ability to analyze heart rhythms, manage airways, initiate intravenous therapy, read and interpret electrocardiograms, and understand emergency pharmacology.

Accordingly, only qualified health care providers (e.g., physicians, pharmacists, midlevel practitioners, respiratory therapists, nurses, and paramedics) understand and operate advanced life support systems. Due to these technical and medical requirements, along with high financial costs, advanced life support systems become impractical for at-home patient care.

DETAILED DESCRIPTION

An exemplary system and method may include a management application that automatically generates an alert in response to receiving a sensor signal indicating patient inactivity or unconsciousness.

A patient typically produces measurable amounts of physiological movement. Physiological movement may be a movement characteristic of or appropriate to a normal functioning organism. An unexpected change in a pattern of such movement may be an indication of patient distress.

For example, the physiological movement of a patient may include the change in shape of a torso as lungs expand and contract during breathing. Therefore, as the torso changes in shape, a corresponding change in pressure distribution by the torso on a surface may be measured or monitored.

An exemplary system and method may thus utilize a sensor system to generate a sensor signal based on the physiological movement of a patient (e.g., a pressure distribution by the torso on a contact surface of the sensor system). The exemplary system and method may further utilize a management application of a computer system to analyze the sensor signal for movement anomalies or inactivity indicative of unconsciousness or death.

Figure 1:
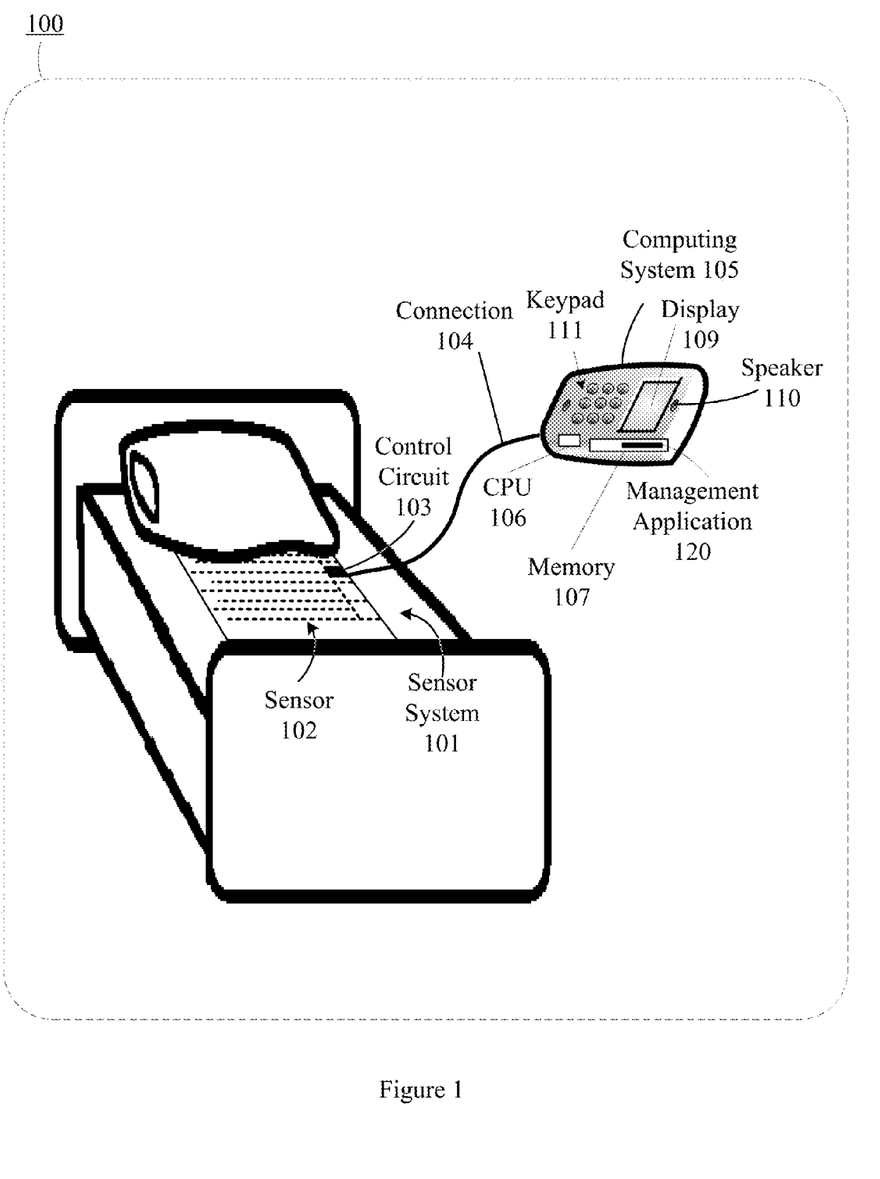
FIG. 1 illustrates an exemplary system in which physiological movements are detected.

FIG. 1 illustrates an exemplary system 100 (e.g., an at-home integrated system) having sensor system 101, which includes at least one of a plurality of sensors 102 and a control circuit 103, connected via a connection 104 to a computing system 105 including a central processing unit (CPU) 106 and a memory 107 with a management application 120 installed thereon. Further, computing system 105 may also include output devices, such as a display 109 and a speaker 110, along with an input device, such as a keypad 111, mouse, touch-screen, microphone, and the like.

The exemplary systems shown in the figures may take many different forms and include multiple and/or alternate components and facilities, and while the exemplary systems are shown in the figures, the exemplary components illustrated in the figures are not intended to be limiting. Indeed, additional or alternative components and/or implementations may be used. For example, the exemplary system 100 and the computing system 105 may be equipped with additional output devices, such as a speaker 110 and/or vibration or electric shock systems, messaging programs, etc., to produce an alert. Further, although the computing system 105 is illustrated as connected via the connection 104 to the sensor system 101, the sensor system 101 and the computing system 105 may also be fully integrated and self-contained within a single device or housing. Also, the components of the exemplary system 100 may be independently located in separate devices or housings, as further described below.

As illustrated in FIG. 1, the control circuit 103 works in conjunction with the sensors 102 to convert pressure distributions of a patient in contact with the sensor system 101 into electrical signals and to generate a sensor signal based on the electrical signals. The sensor signal may be transmitted by the control circuit 103 through the connection 104 to the computing system 105. The management application 120 of computing system 105 may analyze the sensor signal for pressure distribution patterns (e.g., consistencies and variation in the distribution patterns). The management application 120 may also produce visual and auditory representations by a display 109 and a speaker 110 indicating a patient status (e.g., stable/consciousness or alert/unconsciousness) based on the pressure distribution patterns.

For example, when an unexpected pattern of change or lack of physiological movement indicating possible patient distress (e.g., unconsciousness or impending death) is detected by the sensor system 101, the computing system 105 may present an interface on the display 109 and a tone via the speaker 110 to alert the patient back to consciousness. When the patient awakes, the patient may type a passcode via an input such as the keypad 111 to disable the alert.

The illustrative sensor system 101 may include electronic circuitry, such as a plurality of sensors 102, which detects and converts one form of energy, such as mechanical energy, to another form, such as electrical energy. Examples of energy that the sensor system 101 may convert or produce include mechanical energy, elastic energy, sound energy, thermal energy, chemical energy, electric energy, and the like. In addition, the size and shape of the sensor system 101 may vary according to the patient and application, and the sensor system 101 may be configured to attach or conform to a patient or a mating surface. For example, patient comfort may be considered when placing the sensor system 101 between a patient and a surface (e.g., on a bed surface), such as constructing a sensor system 101 from a conductive rubber material integrated with a feather pad.

A sensor (e.g., at least one of a plurality of sensors 102) may be a transducer that outputs an electrical signal in accordance with a particular form of energy. Examples of the plurality of sensors 102 include but are not limited to tactile sensors, vibration powered generators, load cells, strain gauges, or the like and may be constructed from but not limited to conductive rubber, metallic capacitive sensing elements, and the like.

For example, a tactile sensor may be a conductive rubber transducer that outputs an electrical signal in accordance with a pressure (e.g., an object contact force) applied perpendicularly to a contact area (e.g., a local portion of a contact surface) of the tactile sensor. That is, as the tactile sensor compresses and decompresses due to pressure increases and decreases, an electrical capacitance or resistance of the tactile sensor changes. The change in electrical capacitance or resistance is measured and outputted as an electrical signal.

The sensor system 101, as illustrated in FIG. 1, may be a plurality of sensors 102 configured to form an overall sensor array or grid configured for placement between a patient and a corresponding surface. To avoid potentially false readings the mating surface may be formed to minimize an independent input into a sensor. For example, the surface may be inelastic and rigid (e.g., "hard") so that it is permanently fixed in space as compared to the physiological movement of a patient. Therefore, the plurality of sensors 102 may be a tactile sensor array where each tactile sensor in the array detects local pressure changes from patient movement with reference to the corresponding surface. In turn, each tactile sensor in the array generates a local electrical signal that is compiled with the other local electrical signals by a control circuit 103 to generate a sensor signal.

The sensor system 101 may further include a control circuit 103 configured to process electrical signals from the plurality of sensors 102. The control circuit 103 may be a set of electronic circuits on a semiconductor material. The control circuit 103 may be configured to receive and compile electrical signals from each tactile element of the plurality of sensors 102 into a sensor signal (e.g., the control circuit 103 generates a sensor signal in relation to the pressure imposed on the plurality of sensors 102 by the physiological movement of a patient). The control circuit may be configured to transmit the sensor signal to the computing system 105 via a connection 104. The control circuit 103 may also be configured to govern other electrical and mechanical operations, such as to control the mechanisms of an administration device that automatically administers treatment or medicine.

Thus, the sensor system 101 may include a plurality of sensors 102, which form a tactile sensor array, to detect physiological movement of a patient (e.g., pressure changes based on a moving torso), whereby the control circuit 103 may generate a sensor signal compiled from electrical signals generated by the plurality of sensors 102.

A connection 104 may be a wired or wireless connection between two endpoints (e.g., the control circuit 103 and the computing system 105) that carries signals. Although FIG. 1 illustrates the connection 104 as a wire, the connection 104 may also be a wireless connection, as further illustrated by FIG. 2.

A computing system 105 may be any computing system with a central processing unit (CPU) 106 and a memory 107 with a management application 120 installed thereon, where the management application 120 is configured to retrieve and analyze the sensor signal to provide an 'image' of a contact surface between the patient and the sensor system.

Computing systems and/or devices, such as exemplary computing system 105, may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., the BlackBerry OS distributed by Research In Motion of Waterloo, Canada, and the Android operating system developed by the Open Handset Alliance. Examples of computing devices include, without limitation, a smartphone, a mobile phone, a tablet device, a computer workstation, a server, a desktop, notebook, laptop, or handheld computer, or some other computing system and/or device.

Computing systems and/or devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc.

Further, in some examples, computing system 105 elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

In general, a processor or a microprocessor (e.g., CPU 106) receives instructions from a memory (e.g., memory 107) and executes these instructions, thereby performing one or more processes, including one or more of the processes described herein. Such instructions and other data may be stored and transmitted using a variety of computer-readable media. The CPU 106 may also include processes comprised from any hardware, software, or combination of hardware or software that carries out instructions of a computer programs by performing logical and arithmetical calculations, such as adding or subtracting two or more numbers, comparing numbers, or jumping to a different part of the instructions. For example, the CPU 106 may be any one of, but not limited to single, dual, triple, or quad core processors (on one single chip), graphics processing units, visual processing units, and virtual processors. Similarly, control circuit 103 may also be a processor or microprocessor as described above.

The memory 107, in general, may be any computer-readable medium (also referred to as a processor-readable medium) that may include any non-transitory (e.g., tangible) medium that participates in providing data (e.g., instructions) that may be read by a computing system (e.g., by a CPU 106 of a computing system 105). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computing system. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Further, the computing system 105 may include output devices, such as a speaker 110 and/or a display 109, that present auditory or visual information based on a monitoring output generated by the management application. For example, once the sensor signal is retrieved or received by the computing system 105, the management application 120 may analyze the sensor signal to calculate a monitoring output. The monitoring output, in turn, is utilized to generate and present alerts and feedback via an output device.

A display 109 may include any electronic display, which may detect the presence and location of a touch such as a finger or a stylus, for displaying user interfaces, as generated by the management application 120. Examples of an electronic display include liquid crystal displays, cathode ray tubes, etc.

A speaker 110 may include any electric-to-acoustic transducer or sensor that converts an audio stream (e.g., an audio sample or electrical signal) to a sound wave. Examples of speakers may include passive loudspeaker systems, powered loudspeaker systems, fully active loudspeaker systems, and combinations thereof.

A keypad 111, also known as a keyboard, may be an input device that may include a set of buttons that bear digits, symbols, and/or alphabetical letters. Examples of where keypads 111 may be found include calculators, push-button telephones, combination locks, digital door locks, etc. Further, other examples of input devices may include and are not limited to a mouse, a touchscreen, a microphone, and the like.

A management application 120 may be software stored in the memory 107 of the computing system 105 that, when executed by the CPU 106 of the computing system 105, generates and stores patient profiles 241 (illustrated and discussed in more detail with reference to FIG. 2). The management application 120 may store, manage, and execute monitoring heuristics according to patient profiles. For example, the management application 120 may employ the monitoring heuristics to analyze a received sensor signal in support of detecting patient movement anomalies or inactivity.

Monitoring heuristics are a suite of models and methodologies that utilize a sensor signal as an input to generate a monitoring output according to the patient profile. The monitoring output may be configured to represent relative measurements, such as weight distribution, surface area, duration, and the like, in any unit of measurement and to be utilized by an event detection interface (e.g., user interfaces). Further, the control circuit 103 of the sensor system 101 may also be configured to analyze the sensor signal, in combination with or lieu of the management application 120 of the computing system 105.

A patient profile may be a data structure for managing patient care services particular to a patient. Patient care services may include medical response services or doctor prescribed procedures that may be executed in response to patient movement anomalies or inactivity. The management application 120 generates a patient profile by selecting, associating, and configuring monitoring heuristics congruent with the patient care services particular to the patient. The patient profile may be identified by a unique identifier (e.g., patient name or identification number). The patient profile may also be managed and configured via an event detection interface of the management application 120. For instance, the management application 120 may enable the setting of alerts, defining alerts tiers, passcodes, thresholds, location preferences, and the like for a patient profile 241 via the event detection interface. Alert tiers may be a series a ranked alerts configured to enable escalated services or alarms based on patient activity, monitoring heuristics, time durations, and the like.

An event detection interface may be a combination of user interfaces generated by the management application 120. The event detection interface is configured to provide and receive information relative to the patient profiles 241, along with presenting representations of the sensor signal and the monitoring output via a display 109.

An alert is message indicating that a patient movement anomaly or inactivity has been detected by the exemplary system 100. One example of an alert is an alarm sound via the speaker 110 with an intensity that awakes a patient falling into unconsciousness. Alerts may also include mild vibration or electric shock systems that snap a patient away from unconsciousness without harming the patient, a message program that messages an external device or system (e.g., an automatic notification to a 911 call center), or signals a caretaker or service dog, etc.

A passcode is an alpha-numerical combination that disables an alert. In general, when an alert is triggered, a passcode request may be displayed by the display 109. If the correct passcode is entered into the computing system 105 via the keypad 111, the alert is disabled. If a passcode is not entered or an incorrect passcode is entered, then the alert may continue and/or be elevated according to the tiers defined in the patient profile.

A threshold is a predetermined value utilized by the monitoring heuristics to identify patient movement anomalies or unexpected inactivity. For instance, a threshold value may be a fixed duration of time within with the movement anomalies or inactivity may occur before an alert is generated by the management application 120. Also, a minimal change threshold may be a fixed amount of physiological movement deviation that is less than normal movement characteristic (e.g., a measured pressure distribution indicative of a non-breathing patient).

Thus, the exemplary system 100 may provide a management application 120 of a computing system 105 that may retrieve a sensor signal from sensor 101, analyze the sensor signal according to monitoring heuristics associated with a patient profile, and generate a monitoring output that is represented by output devices.

In addition, the sensor system 101, the computing system 105, or both may include a power supply. A power supply may be any power source, such an internal power device consisting of one or more electrochemical cells that convert stored chemical energy into electrical energy and is configured to supply electricity to the components of the exemplary system 100. The power supply may also be a power cord to an external power source in combination with or lieu of the internal power device. Further, when a power supply is not included in or connected to a first component of the exemplary system 100, electricity may be supplied to the first component from a second component via any connection.

Figure 2:
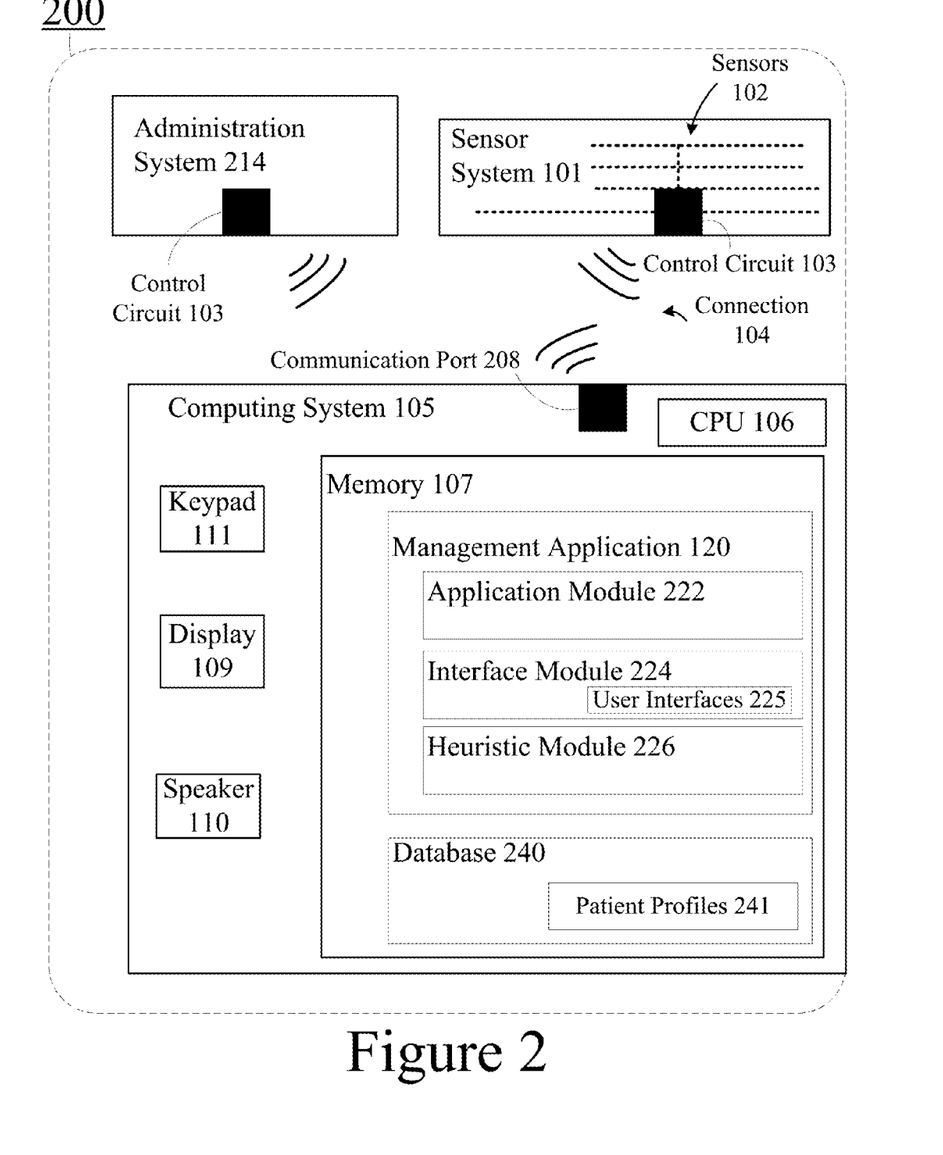
FIG. 2 illustrates an exemplary system that includes a management application installed on a memory of a computing system that generates a monitoring output based on a sensor signal.

FIG. 2 illustrates an exemplary system 200 (e.g., an at-home mobile device system) that includes a sensor system 101, a computing system 105, and an administration system 214. Note that the same or equivalent elements as those of the FIG. 1 described above are denoted with similar reference numerals, and will not be described in detail with regard to FIG. 2.

As illustrated in FIG. 2, the computing system 105 may also include a communication port 208 and the memory 107 of computing system 105 may further store a management application 120 comprising an application module 222, an interface module 224 (which generates user interfaces 225), and a heuristic module 226 along with a database 240 (which manages patient profiles 241).

In general, the exemplary system 200 utilizes the management application 120 to manage patient profiles 241, analyze sensor signals, and generate monitoring outputs in support of detecting patient movement anomalies or inactivity. That is, the computing system 105 may retrieve or receive via a communication port 208 and connection 104 a sensor signal generated by the sensor system 101. The application module 222 of the management application 120 processes and forwards the sensor signal to the heuristic module 226. The heuristic module 226 utilizes patient profiles 241 to select and apply monitoring heuristics to the sensor signal, which in turn generates a monitoring output. The management application 120 utilizes the monitoring output to generate and display via the interface module 224 a user interface 225 on a display 109 indicating the status of the patient and/or to produce and supply via the application module 222 an electronic signal to the speaker 110 to sound an alert.

The communication port 208 may include any connector used for digital or analog signal transfers. For instance, the communication port 208 may be any antenna technology that implements a wireless exchange of data, such as cellular, Bluetooth®, or the like, by converting propagating electromagnetic waves to and from conducted electrical signals. For example, the communication port 208 may be an antenna technology that implements Wi-Fi, which is used to exchange data wirelessly using radio waves over a short range network, as described below.

The administration system 214 may be any system or device that is connected to the patient and automatically administers treatment or medicine. An example of an administration system 214 may be an intravenous (IV) infusion device or pump, which controls the rate at which IV fluids and/or IV medications are administered to a patient. An example of an administration system 214 may also be a report generating device that produces reports detailing instructions for patient care, such as an increase in medication.

The management application 120, which comprises the application module 222, the interface module 224, and the heuristic module 226, may further be configured to manage patient profiles, receive or retrieve a sensor signal, analyze the sensor signal according to monitoring heuristics associated with a patient profile 241, and generate a monitoring output in support of visual and auditory representation by a display 109 and speaker 110, such as a user interface 225 (e.g., an event detection interface) or an alert sound.

The management application 120 through its modules may enable patient profiles 241 to be generated, configured, and stored in the database 240. The management application 120 utilizes the application module 222 and/or interface module 224 to select, associate, and configure monitoring heuristics with the patient profiles 241.

The management application 120 through its modules may retrieve a sensor signal via the communication port 208. For example, when the electrical signals related to the natural expanding and contracting of a breathing torso are processed by the sensor system 101, the application module 222 may retrieve the sensor signal via the communication port 208 and supply it to the heuristic module 226 for analysis.

Further, the management application 120 through its modules may analyze sensor signals in accordance with a selected or preloaded patient profile 241. For example, the heuristic module 226 may perform an analysis by applying the monitoring heuristics associated with the selected or preloaded patient profile 241 to the sensor signal. Thus, based on the configuration of the alerts, passcodes, thresholds, and the like of a patient profile 241, the management application 120 may detect or target specific patient movement anomalies or inactivity within the sensor signal.

The management application 120 through its modules may also generate a monitoring output. For instance, the management application 120 may generate electronic signals that trigger an alarm sound, a vibration or electric shock system, a message, etc. Further, the management application 120 may also integrate the monitoring output with user interfaces 225 (e.g., an event detection interface) and provide the integrated interfaces to a display local or external to the computing system 105.

In addition, although FIG. 2 illustrates modular examples of the management application 120, where the modules 222, 224, and 226 may be software that when executed by the CPU 106 provides the operations described herein, the management application 120 and its modules 222, 224, and 226 may also be provided as hardware or firmware, or combinations of software, hardware and/or firmware. Additionally, although one exemplary approach to the modularization of the management application 120 is illustrated and described, the operations thereof may be provided by fewer, greater, differently named, or differently located modules.

An application module 222 may include program code configured to facilitate communication between the modules of the management application 120 and hardware/software components external to the management application 120. For instance, the application module 222 may include program code configured to communicate directly with other applications, modules, models, devices, and other sources through both physical and virtual interfaces. That is, the application module 222 may include program code and specifications for routines, data structures, object classes, and variables that package and present data received from user interfaces 225 generated by the interface module 222 for transfer over a network or through a connection, as further described below. In one illustrative approach, the application module 222 may include program code for communication with a sensor system 101 and sending information to systems external to system 200 (e.g., the application module 222 may retrieve the sensor signal from the communication port 208 and supply it to the heuristic module 226 for analysis).

An interface module 224 may include program code for generating and managing user interfaces 225 that control and manipulate the management application 120 based on a received input. User interfaces 225 may enable the selecting and configuring of monitoring heuristics and patient profiles 241. For instance, the interface module 224 may include program code for generating, presenting, and providing one or more user interfaces 225 (e.g., in a menu, icon, tabular, map, or grid format) in connection with other modules for providing information (e.g., data, notifications, counters, instructions, etc.) and receiving inputs (e.g., patient profile 241 and monitoring heuristic configurations). The interface module 224 may also display user interfaces 225, such as the event detection interface described above, to a display that present information relative to the patient profiles, along with representations of the received sensor signal and the monitoring output.

Moreover, user interfaces 225 described herein may be provided as software that when executed by the CPU 106 provides the operations described herein, such as displaying a representation on a display 109 indicating a status (e.g., stable/consciousness or alert/unconsciousness) of the patient based on the pressure distribution patterns. The user interfaces 225 may also be provided as hardware or firmware, or combinations of software, hardware, and/or firmware.

The heuristic module 226 may include program code configured to store, manage, and execute monitoring heuristics according to patient profiles. The heuristic module 226 may also include program code configured to utilize the monitoring heuristics to analyze a sensor signal to determine physiological movements and variations thereof (e.g., pressure distributions and changes imposed on the sensor system 101 over time).

For example, the physiological movement of a patient may include physical change of a torso as lungs expand and contract during breathing. The natural expanding and contracting of a torso alters with reference to a corresponding surface the pressure distribution on the tactile sensors of sensor array 102, which in turn may supply electrical signals to the control circuit 103. The control circuit 103 processes the electrical signals and transmits a sensor signal to the communication port 208. The sensor signal is utilized by the heuristic module 226 as an input to a monitoring heuristic, which compares the sensor signal to a minimal change threshold. If the monitoring heuristic indicates that a change in pressure distribution remains at a level greater than or equal to a minimal change threshold, the management application 120 identifies the patient as breathing (e.g. status is stable). If the monitoring heuristic indicates that the change in pressure distribution is less than a minimal change threshold, the management application 120 identifies the patient as not breathing and triggers an alert. Thus, the monitoring heuristic may apply minimal change thresholds and duration restrictions as directed by a patient profile 241 to distinguish breathing from not breathing.

An example of a monitoring heuristic includes the following Heuristic A, as written in the programming language C++:

```
int main ( )
{
  do
  {
    int C = 0;
    int X = 10;
    cout << "stable",
    do
    {
      C + +;
      if(C ≥ X)
      {
        cout << "alert";
      }
    }while(ΔS < P);
  }while(ΔS ≥ P);
  return 0;
}
```

In Heuristic A, 'int' is a fundamental type of the programming language C++ used to define numeric variables holding whole numbers and is short for integer. 'int main( )' is a special function of the programming language C++ that signifies the start of a program or heuristic. 'do{ }while( )' is a function of the programming language C++ that repeats a statement a certain number of times or while a condition is fulfilled. 'C' is a integer counter that increments when a change in a pressure distribution 'ΔS' is less than a minimal change threshold 'P.' 'X' is a integer threshold value equal to a fixed duration of time that movement anomaly or inactivity may be tolerated before an alert is generated by the management application 120. 'cout' is an object of the programming language C++ that represents a standard output stream.

'stable' is an output of the Heuristic A while 'ΔS' remains at a level greater than or equal to a minimal change threshold 'P.' When 'stable' is output by the Heuristic A, the heuristic is representing that a patient is exhibiting pressure distribution patterns indicative of proper physiological movement.

'C++' is a function of the programming language C++ that represents an incrementing integer. 'if{ } ' is a function of the programming language C++ that executes a statement when a condition is fulfilled. 'alert' is an output of the Heuristic A while 'ΔS' is less than a minimal change threshold 'P. When 'alert' is output by the Heuristic A, the heuristic is representing that a patient is exhibiting pressure distribution patterns lacking proper physiological movement.

'ΔS' is a change in a pressure distribution over time as detected by the sensor system 101, where time is a predefined interval. 'P' is minimal change threshold equal to a fixed amount of pressure deviation that is less than normal movement characteristic. Note that the integer threshold value 'X,' the minimal change threshold 'P,' and the predefined time interval may be constants defined by a selected or preloaded patient profile 241.

In exemplary Heuristic A, the counter 'C' is set to zero, and the integer threshold value 'X' is set to 10. The monitoring output is "stable" while the change in pressure distribution 'ΔS' remains at a level greater than or equal to a minimal change threshold 'P.' When the change in pressure distribution 'ΔS' is less than a minimal change threshold 'P,' the counter 'C' will increment until the change in pressure distribution 'ΔS' returns to at a level greater than or equal to a minimal change threshold 'P.' Yet, if the counter 'C' matches or exceeds the integer threshold value 'X,' then exemplary Heuristic A outputs an "alert."

Note that the loop may be governed by various clock cycles such that the counter 'C' may increment at specific intervals as further described below. For instance, the integer threshold value 'X' may be set to an integer 10 so that an "alert" is triggered when the change in pressure distribution 'ΔS' has less than a minimal change threshold 'P' for at least after 10 loops (e.g., 10 clock cycles).

Another example of a monitoring heuristic includes the following Heuristic B, as written in the programming language C++:

```
int main ( )
{
  do
  {
    char passcode[4];
    int Y = 1983;
    int C = 0;
    int X = 15;
    cout << "stable";
    do
    {
      C + +;
      if(C ≥ X)
      {
        cout << "alert";
        cin >> passcode;
        if(Y ≠ passcode)
        {
          cout << "alert - incorrect passcode";
        }
        if (Y == passcode)
        {
          break;
        }
      }
    }while (ΔS < P);
  }while(ΔS ≥ P);
  return 0;
}
```

Similar to heuristic A, Heuristic B includes a counter 'C,' a change in pressure distribution 'ΔS,' a minimal change threshold 'P,' and a integer threshold value 'X.' In addition, Heuristic B includes a character sequence input 'passcode,' and predefined four digit number 'Y.' 'char' is a fundamental type of the programming language C++ used to define an alpha-numeric array for character sequence. 'cin' is an object of the programming language C++ that represents the standard input stream.

In exemplary Heuristic B, the counter 'C' is set to zero and the monitoring output is "stable" while the change in pressure distribution 'ΔS' remains at a level greater than or equal to a minimal change threshold 'P.' Further, a 'char' is defined as a four character sequence identified by 'passcode,' the integer threshold value 'X' is set to 15, and the predefined four digit number 'Y' is set to 1983.

Thus, when the change in pressure distribution 'ΔS' is less than a minimal change threshold 'P' and the counter 'C' matches or exceeds the integer threshold value 'X,' then the heuristic outputs an "alert" and awaits a character sequence input 'passcode' to be entered. If the character sequence input 'passcode' is entered incorrectly (e.g., Y≠passcode), then Heuristic B remains in "alert" mode. If the character sequence input 'passcode' is entered correctly (e.g., Y=passcode), then the alert loop is broken and Heuristic B returns to monitoring the change in pressure distribution 'ΔS.'

In Heuristic B, the integer threshold value 'X' may be set to an integer 15 so that an "alert" is triggered when the change in pressure distribution 'ΔS' has less than a minimal change threshold 'P' for at least after 15 loops (e.g., 15 clock cycles). Note that a value of the integer threshold value 'X' may be manipulated via the management application to be a value equivalent to a time duration. For instance, if 40 algorithm loops are equal to 1 second, then to implement a timer of 5 seconds the integer threshold value 'X' may be set to 200. Thus, timing durations, such as 5 seconds, 10 seconds, 20 seconds, 40 seconds, etc., may be received via the management and utilized to set a corresponding value for the integer threshold value 'X'.

Further, the heuristic module 226 and the management application 120 may be programmable. For instance, the management application 120 may be set to a learning mode where patterns of pressure distribution are logged (e.g., in a table) and used by the heuristic module 226 to detect discrete variations. The logged patterns or components thereof (e.g., such as pressure durations) may be associated to a patient profile along with a patient's size, weight, gender, and/or age. These metrics may then be used to by the management application 120 to enhance and improve the accuracy of existing monitoring heuristics.

In addition, constants (e.g., the integer threshold value 'X' and the minimal change threshold 'P') may have a predetermined maximums or minimums such that, regardless of a patient profile metrics, the monitoring heuristics may output an alert. Further, multiple constants and counters may be utilized by the heuristic module 226 to output different alerts or identify different patient conditions outside of a change of physiological movement. Note that counters may also decrement, as well as increment.

A database 240 may include any type of data or file system (e.g., patient profiles 241) that operates to support the management application 120. For instance, the patient profiles 241 may include patient health information, patient physical specifications, alert condition information, threshold values related to alert conditions, patient care services, passcodes, messages, instructions, etc.

In general, databases, data repositories or other data stores, such as database 240, described herein may include various kinds of mechanisms for storing, providing, accessing, and retrieving various kinds of data, including a hierarchical database, a set of files in a file system, an application database in a proprietary format, a relational database management system (RDBMS), etc. Each such data store may generally be included within a computing system (e.g., computing system 105 or databases 240a-b, as described below) employing a computer operating system such as one of those mentioned above, and are accessed via a network or connection in any one or more of a variety of manners. A file system (e.g., patient profiles 241) may be accessible from a computer operating system, and may include files stored in various formats. An RDBMS generally employs the Structured Query Language (SQL) in addition to a language for creating, storing, editing, and executing stored procedures, such as the PL/SQL language mentioned above.

Figure 3:
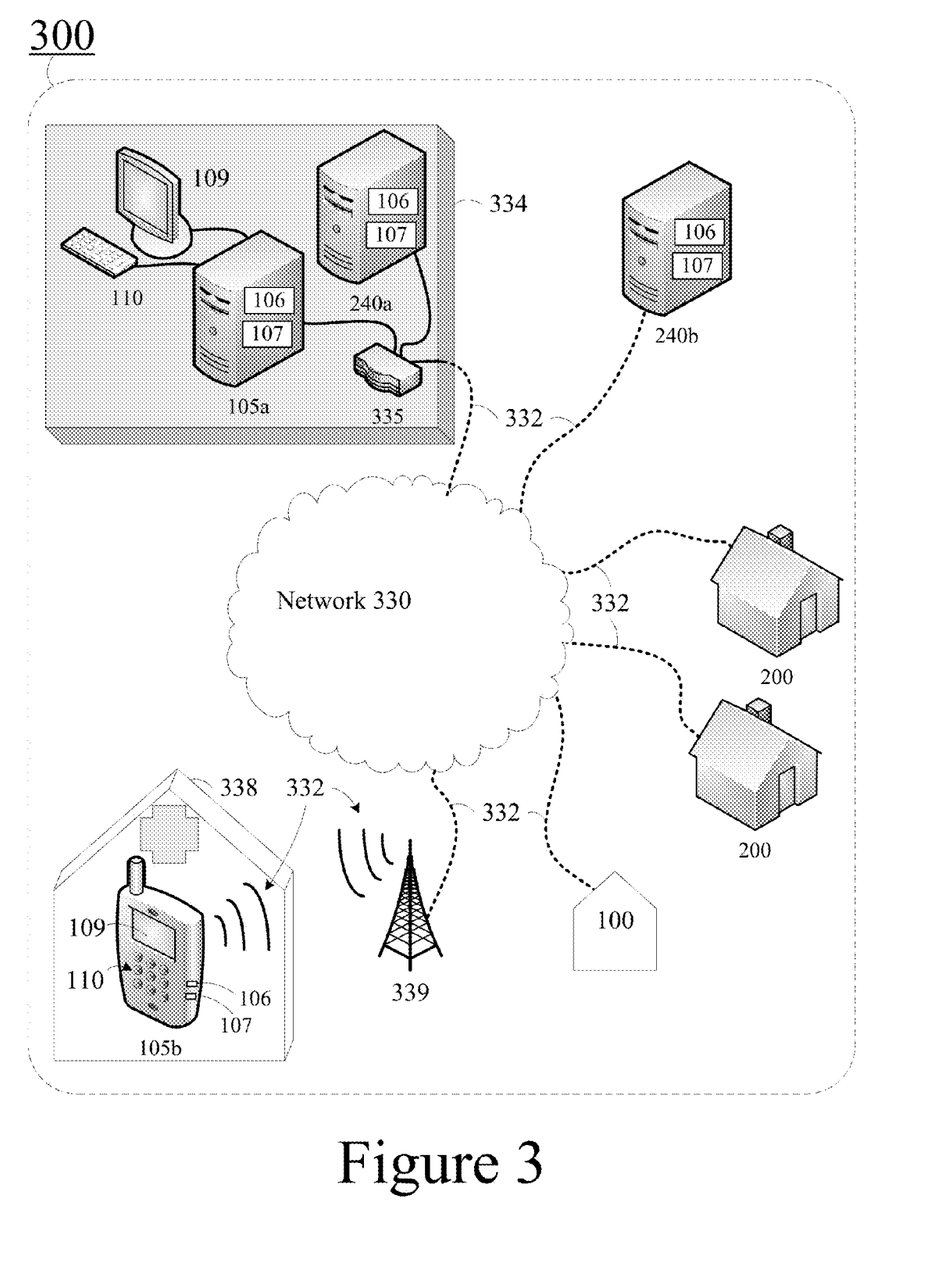
FIG. 3 illustrates an exemplary system that includes multiple computing systems, databases, and at-home systems.

In addition, as indicated in FIG. 2, database 240 includes patient profiles 241 and may be provided as software stored on the memory 107 of computing system 105. The database 240 may also be provided as hardware or firmware, or combinations of software, hardware and/or firmware. For example, as indicated in FIG. 3, databases 240a-b may be a computing device, as described above, including a CPU and memory that is separate from a computing system 240a-b.

Thus, in view of the above, the exemplary systems and methods may be implemented as an at-home integrated system (e.g., exemplary system 100) where the computing system 105 may be a control device attached to a sensor pad and operated by the patient in contact with the sensor system 101 or a caretaker locally present to the patient.

Additionally, the wired connection 104 of the control device in the at-home integrated system may be detachable thereby enabling the control device to communicate wirelessly to form an at-home mobile device system (e.g., exemplary system 200).

In the at-home integrated system and the at-home mobile device system, the computing system 105 (e.g., the control device) may store and utilize local patient profiles 241 locally. Further, the computing system may also receive patient profiles 241 along with updates to the management application 120 and other system resources may be pulled from an external source or a remote location (e.g., a user profile that was already established at a hospital). For example, a detachable control device may be a mobile device, such as a smart phone that may download the management application 120 from a database external to an exemplary system 100, 200.

For example, the at-home integrated system and/or at-home mobile device system may be integrated into a monitoring management (e.g., exemplary monitoring service 300).

FIG. 3 illustrates an exemplary monitoring service 300 having multiple computing systems, databases, and at-home systems. For instance, the exemplary monitoring service 300 may have computing systems 105a-b and databases 240a-b, each of which includes a CPU 106 and a memory 107. Further, exemplary monitoring service 300 also illustrates a network 330, connections 332, a central office 334, a network device 335, a medical facility 338, a tower 339, at-home integrated system 100, and at-home mobile device systems 200.

In general, a central office 334 manages and supplies data relative to patients located in at-home systems 100, 200. Further, the exemplary monitoring service 300 may enable qualified medical personnel located at a medical facility 338 and operating connected computing systems, such as computing system 105b, access to the information and data within the central office 334 in support of providing patient care services. Thus, in the exemplary monitoring service 300, the patients located in the at-home systems 100, 200 may receive medical attention from their at-home caretaker along with their physician and/or medical service provider.

Note that the same or equivalent elements as those of the FIGS. 1 and 2 described above are denoted with similar reference numerals, and will not be described in detail with regard to FIG. 3. In addition, exemplary monitoring service 300 may take many different forms and include multiple and/or alternate components and facilities. While an exemplary monitoring service 300 is shown in FIG. 3, the exemplary components illustrated in FIG. 3 are not intended to be limiting. Indeed, additional or alternative components and/or implementations may be used.

A network 330 may be a collection of computers and other hardware to provide infrastructure to carry communications. For instance, the network 330 may be an infrastructure that generally includes edge, distribution, and core devices and provides a path for the exchange of information between different devices and systems (e.g., between the computer system 105b and database 240b).

Further, the network may employ any networking technology. For instance, network 330 may, in general, be any packet network (e.g., any of a cellular network, global area network, wireless local area networks, wide area networks, local area networks, or combinations thereof, but may not be limited thereto) that provides the protocol infrastructure to carry communications between multiple computing systems, databases, and at-home systems.

Connections 332 may be wired or wireless connections between two endpoints (devices or systems) that carry electrical signals that facilitate virtual connections. Virtual connections are the protocol infrastructure that may enable communication to and from the multiple computing systems, databases, and at-home systems of FIG. 3.

A central office 334 may be a location of a medical service provider. The central office 334 may perform the role of a monitor device or facility that gathers and forwards data in support of providing medical and emergency services, along with detecting or receiving location information for at-home systems and hospital systems (e.g., the at-home systems 100, 200). For example, if a patient located in one of the at-home systems 100, 200 were to exhibit improper physiological movement for a period longer than a designated duration, the central office 334 and its systems may actively analyze the respective at-home systems 100, 200 and execute alerts according to a patient profile 241. For instance, the central office may automatically contact a patient's physician, an emergency contact, or a 911 responder based upon the data within a patient profile 241.

Further, if a patient and the at-home system were to move to a new geographic location (e.g., move from a patient residence to a relative's residence), the monitoring device may detect or receive location information of the at-home system via location determination technologies. Examples of location determination technologies may include network-based, handset-based, SIM-based, global positioning or any similar location systems, such as a locator application installed on a smartphone of the at-home system that uploads location information to the monitoring device based on a network location within the system 300. Therefore, once the location information of the at-home system is determined, the monitoring device may utilize the location information in conjunction with the patient profile 241 to automatically contact local emergency services and direct those service to a correct location.

The central office 334 may also manage and transfer patient profiles 241 along with management application 120 updates for at-home systems and hospital systems. For example, the central office may transfer patient profiles 241, management application updates 120, and the like to the at-home integrated system 100 and the at-home mobile device systems 200 and enable the downloading of the same for use in a medical facility 338, etc. Thus, the central office 334 may be configured to provide two-way communications of information based on a collective assembly of knowledge and best practices for a particular patient.

The central office 334 may generally include a computing system 105a which performs server operations for computing systems that do not have a full management application installed thereon. That is, the computing systems 105a may provide operational use of its resources to computing systems outside of the central office 334. The central office 334 also includes a database 240a, which is separate from computing system 105a and which communicates with the computing system 105a to supply the full operational capabilities of a management application. Further, the central office 334 may automatically compile patient profiles to enhance the monitoring heuristic employed by the management application across the exemplary monitoring service 300. For example, the central office 334 may pull information from multiple patient profiles 241 and at-home systems 100,200 to determine long term trends and refinements for monitoring (e.g., quality control regarding setting heuristic parameters, such as weight, age, gender, etc.).

In addition, the central office may utilize a redundant system in database 240b. Further, database 240b is available to computing systems that either cannot access the necessary resources at the central office 334 or that are particular assigned to the database 240b. For instance, computing system 305b may be assigned to access data and information directly from database 240b in support of supplying medical services to at-home systems 300.

A network device 335 may be a computing system as described above and, more particularly, may be an edge, a distribution, or a core device that is a path gateway between the network 330 and central office 334.

A medical facility 338 may be a hospital, a location for emergency services, or a location of a patent's physician. The medical facility 338 may also perform the role of a monitor device or facility that may immediately respond to an indication that a patient is exhibiting improper physiological movement for a period longer than a designated duration.

A tower 339 may be a tall structure designed to support antennas or aerials for telecommunications along with communication ports for additional computing systems. Thus, the tower 339 may enable wired or wireless connections 332 that carry signals to or from the network 330 (e.g., a connection from the network 330 via the tower 339 to the computing system 305b). For example, the tower 339 may enable a computing system 305b to connect to and access the systems, devices, and data associated with the network 330 providing the computing system 305b is location within the range of tower 339.

Database 240a-b may be computing systems, as further described above with reference to database 240 of FIG. 2. Note that database 240b, although illustrated as not physically located within the central office 334, the medical facility 338, or at-home systems 200, the database 240b may nevertheless be integrated with any one of the central office 334, the medical facility 338, or at-home systems 200. Thus, although a computing system may not be at the same location as database 240b, the computing system may still access data and information stored on database 240b via the network 330.

At-home systems 100, 200 are similar to the exemplary system 100, 200 described, where each the at-home systems 100, 200 includes a distinct patient with a distinct patient profile that is being monitored by a sensor and a computing system. In addition, the computing systems of the at-home systems 100, 200 may also be referred to as a partner device.

A partner device is any computing device described above. More particularly, a partner device may be a smartphone with a management application installed thereon. The partner device, in general, remains in the possession of an at-home caretaker, so that the at-home caretaker may be alerted of patient movement anomalies or inactivity by the partner device. Additionally, a partner device may also connect with multiple at-home systems 100, 200 across the network 330 such that any alert produced by the at-home systems 100,200 may be received by the partner device.

Further, the partner device may communicate the sensor data to a monitor device (e.g., computing systems 305a-b). For example, partner devices may be enabled by machine to machine communication to be wirelessly coupled with a sensor while being networked with a monitor device. In this manner, the monitor device may respond based on activity of the partner devices and sensor systems.

One exemplary response may be that the monitoring device generates reports based on the activity, and, due to the reports, real-time medical decisions may be communicated and/or real-time emergency pharmacology may be executed.

For example, an administration device such as an IV pump may be connected to the patient and networked with a partner device. When a report generated by a monitor device indicates that a patient requires an increase in medication, a medical decision to increase the medication may be made and communicated to the partner device. The partner device in response may trigger the IV infusion pump to increase the rate at which IV medication is administered.

Another example may include a patient exhibiting improper physiological movement for a period longer than a first designated duration (as configured in the patient profile 241) with the monitoring device entering into a tier one alert that permits the patient or caretaker time to enter a passcode and disable the alert. If the tier one alert were to continue for a period longer than a second designated duration the monitoring device may automatically contact a patient's physician, an emergency contact, or a 911 responder based upon the data within a patient profile 241.

Figure 4:
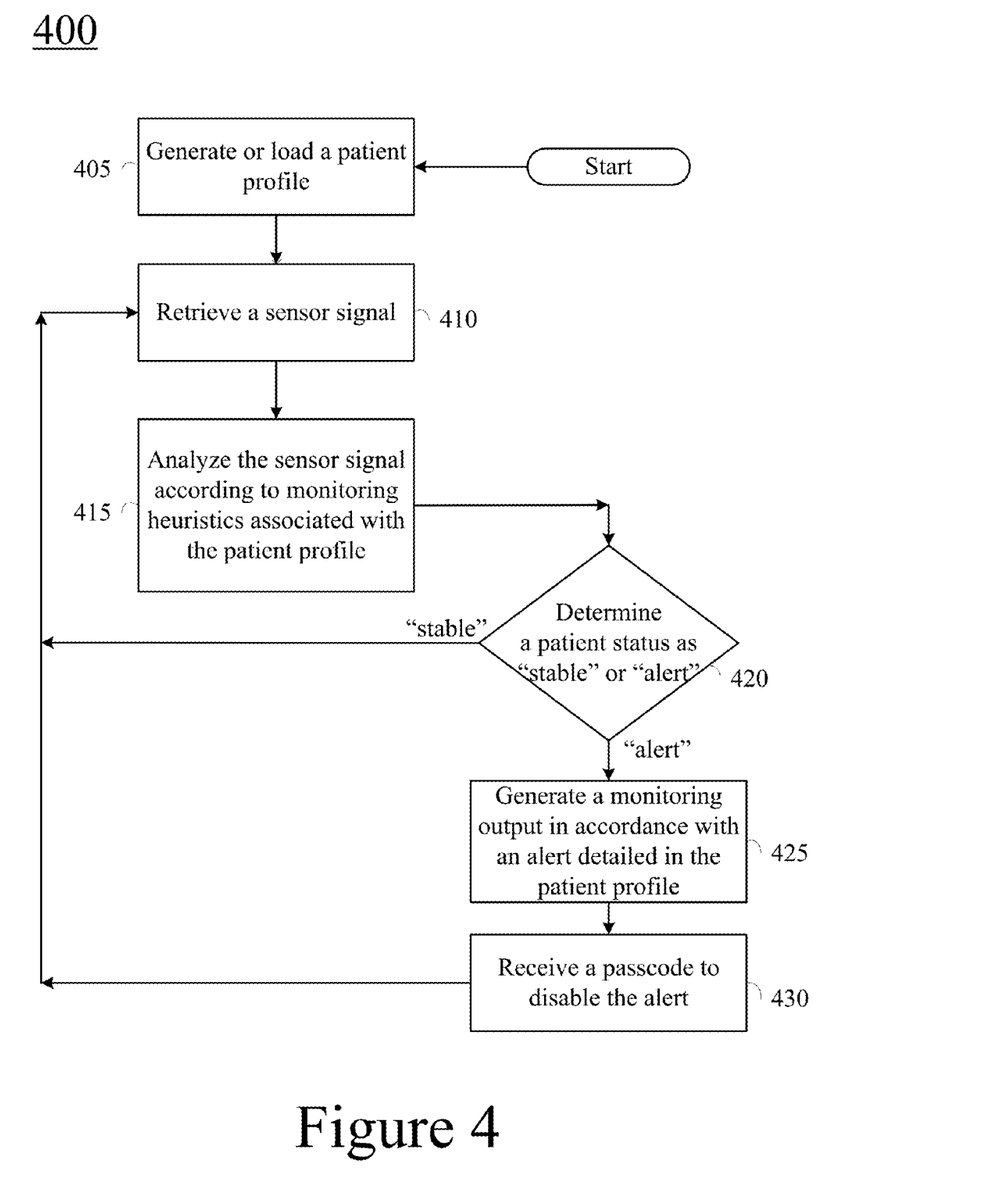
FIG. 4 illustrates an exemplary process flow executed by a management application.

FIG. 4 illustrates an exemplary process flow 400 executed by the management application 120 to generate 405 or load patient profiles, retrieve 410 a sensor signal, analyze 415 the sensor signal according to monitoring heuristics associated with the patient profile, and determine 420 a patient status, where a "stable" status returns the process flow 400 to retrieving 410 a sensor signal and an "alert" status triggers the management application 120 to generate 425 a monitoring output and receive 430 a passcode to disable the monitoring output.

The process flow begins by proceeding to block 405 where, for example, the management application 120 generates or loads a patient profile. In the case of generating a patient profile, the management application 120 receives an input via a user interface 225 of the interface module 224 that includes a unique identifier and patient metrics. The management application 120 utilizes the unique identifier and the patient metrics to generate a shell data structure. The management application 120 associates monitoring heuristics with the shell data structure and prompts for further input through the user interface 225 regarding setting alerts, passcodes, thresholds, and the like. Note that newly generated patient profiles are loaded into the management application 120 and stored in a database 240 after generation.

In the case of loading a patient profile, the management application 120 utilizes an application module 222 to access the patient profiles 241 within a database 240 and populates a user interface 225 via the interface module 224 with the accessed patient profiles 241. The management application 120 receives an input via a user interface 225 identifying which patient profile 241 to load. In this manner, a selected patient profile 241 is displayed by the user interface for further configuration and associated monitoring heuristics are primed for execution.

In addition, whether a patient profile 241 is generated or loaded, the management application 120 may further update the patient profile by accessing systems external to exemplary system 200 and importing further data (e.g., medical history, doctor instructions, updated monitoring heuristics, etc.).

Next, in block 410, the management application may retrieve a sensor signal. For example, the management application 120 via the application module 222 may retrieve a sensor signal from the communication port 208, which received the sensor signal transmitted from the control circuit 103 over a connection 104. The management application 120 via the application module 222 may also access the control circuit and actively pull a sensor signal over the connection 104 via the communication port 208.

Next, in block 415, the management application may analyze the sensor signal according to monitoring heuristics associated with a generated or loaded patient profile 241. That is, the management application 120 via the heuristic module 226 executes monitoring heuristics utilizing variables and constants specified by a patient profile 241. In this exemplary process flow 400, the management application 120 may modify Heuristic A and B based on the configurations specified in patient profile 241 to generate Heuristic C. Heuristic C is then applied by the management application 120 to the sensor signal.

Utilizing the Heuristic C, the management application 120 determines, in block 420, a patient status. For example, if the change in pressure distribution remains at a level greater than or equal to a minimal change threshold (e.g., $\Delta S \geq P$), then the patient status is "stable" and the exemplary process flow 400 returns to block 410.

If the change in pressure distribution is less than a minimal change threshold (e.g., $\Delta S < P$), then counter increments until the change in pressure distribution returns to at a level greater than or equal to a minimal change threshold. And if the counter increments to a value that matches or exceeds the threshold value (e.g., a duration of time specified in the patient profile 241) while the change in pressure distribution is less than a minimal change threshold, then the patient status is "alert" and the exemplary process flow 400 proceeds to block 425.

In block 425, the management application 120 generates a monitoring output in accordance with the configuration of the patient profile 241. For example, the monitoring output may comprise an alarm sound that awakes the patient; however, the monitoring output may also trigger a vibration or electric shock systems, messaging system, etc. The management application 120 may also integrate the monitoring output with the user interface 225 and display the integrated interface on a display local or external to the computing system 105.

Further, the management application 120 may communicate with other devices, such as a monitor device or an administration device as described above, not included in exemplary system 200. Thus, real-time medical decisions may be communicated to the computing system 105 and/or real-time emergency pharmacology may be executed. After generating a monitoring output, the exemplary process flow 400 proceeds to block 425.

Next, in block 430, the management application 120 receives a passcode via the interface module 224 of the computing system 105 in response to a prompt for a passcode by the user interface 225. In the case where the alarm sound successfully woke a patient from unconsciousness, the patient may to enter the correct passcode via the user interface 225 and disable the alert. Next, the exemplary process flow 400 returns to block 410 and monitoring continues. In other embodiments, instead of a passcode, a fingerprint or other biometric input may be used by the patient.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description or Abstract below, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A system, comprising:
a device including a memory with a management application installed thereon, wherein the management application is configured to:
process a sensor signal generated by a sensor system configured between a patient and a corresponding surface, the sensor signal being configured based on a physiological movement detected by the sensor system;
analyze the sensor signal utilizing a monitoring heuristic associated with a patient profile, wherein the monitoring heuristic is configured to identify physiological movement patterns over time within the sensor signal and generate an output based on the identified physiological movement patterns; and
at least one of:
a) generate the patient profile based on an input received by the device configured to include a unique identifier and patient metrics; associate the monitoring heuristic with the patient profile; modify the monitoring heuristic based on the patient metrics to generate a modified monitoring heuristic; and load the patient profile including the modified monitoring heuristic; and
b) access a patient profile set within the memory; generate a user interface configured to display the patient profile set; and load the patient profile that comprises the monitoring heuristic based on an input received via the user interface configured to identify the patient profile from the patient profile set.

2. The system of claim 1, wherein the management application loads the patient profile by being further configured to:
generate the patient profile based on the input received by the device configured to include the unique identifier and patient metrics;
associate the monitoring heuristic with the patient profile;
modify the monitoring heuristic based on the patient metrics to generate the modified monitoring heuristic; and
load the patient profile including the modified monitoring heuristic.

3. The system of claim 1, wherein the management application loads the patient profile by being further configured to:
access the patient profile set within the memory;
generate the user interface configured to display the patient profile set;
load the patient profile that comprises the monitoring heuristic based on the input received via the user interface configured to identify the patient profile from the patient profile set.

4. The system of claim 1, wherein the sensor system is configured to generate the sensor signal in relation to a detected pressure distribution imposed on a sensor array, and
wherein the physiological movement is a change in the detected pressure distribution over time.

5. The system of claim 1, wherein the management application is further configured to:
modify the monitoring heuristic according to the physiological movement patterns to detect discrete variations in the sensor signal.

6. The system of claim 1, wherein the management application is further configured to determine that a status of the patient is stable when the output indicates that the physiological movement is greater than or equal to a minimal change threshold, and
determine that the status of the patient is alert when the output indicates that the physiological movement is less than a minimal change threshold and that a counter matches or exceeds a threshold time value.

7. The system of claim 1, further comprising:
an administration system configured to control an administration rate of medications based on the output.

8. The system of claim 1, wherein the management application is further configured to:
generate reports based on the output; and
transmit reports to a monitoring system configured to respond with patient care instructions.

9. A method, comprising:
processing a sensor signal generated by a sensor system configured between a patient and a corresponding surface, the sensor signal being based on detecting physiological movement by the sensor system;
analyzing the sensor signal by a monitoring heuristic associated with a patient profile;
identifying, by the monitoring heuristic, physiological movement patterns over time within the sensor signal;
generating, by the monitoring heuristic, an output based on the physiological movement patterns; and
at least one of:
a) generating the patient profile based on receiving an input that includes a unique identifier and patient metrics; associating the monitoring heuristic with the patient profile; modifying the monitoring heuristic based on the patient metrics to generate a modified monitoring heuristic; and loading the patient profiles including the modified monitoring heuristic; and
b) accessing a patient profile set within a computing system; generating a user interface configured to display the patient profile set; and loading the patient profile that comprises the monitoring heuristic based on an input received via the user interface configured to identify the patient profile from the patient profile set.

10. The method of claim 9, further comprising:
generating the patient profile based on receiving the input that includes the unique identifier and patient metrics;
associating the monitoring heuristic with the patient profile;
modifying the monitoring heuristic based on the patient metrics to generate the modified monitoring heuristic; and
loading the patient profiles including the modified monitoring heuristic.

11. The method of claim 9, further comprising:
accessing the patient profile set within the computing system;
generating the user interface configured to display the patient profile set;
loading the patient profile that comprises the monitoring heuristic based on the input received via the user interface configured to identify the patient profile from the patient profile set.

12. The method of claim 9, further comprising:
generating the sensor signal in relation to a detected pressure distribution imposed on a sensor array, wherein the physiological movement is a change in the detected pressure distribution over time.

13. The method of claim 9, further comprising:
modifying the monitoring heuristic according to the physiological movement patterns to detect discrete variations in the sensor signal.

14. The method of claim 9, further comprising:
determining a status of the patient is stable when the output indicates that the physiological movement is greater than or equal to a minimal change threshold, and
determining the status of the patient is alert when the output indicates that the physiological movement is less than a minimal change threshold and that a counter matches or exceeds a threshold time value.

15. The method of claim 9, further comprising:
controlling an administration rate of medications based on the output.

16. The method of claim 9, further comprising:
generating reports based on the output; and
transmitting reports to a monitoring system configured to respond with patient care instructions.

17. A computer-readable medium tangibly embodying computer-executable instructions comprising:
processing a sensor signal generated by a sensor system configured between a patient and a corresponding surface, the sensor signal being based on detecting physiological movement by the sensor system;
analyzing the sensor signal by a monitoring heuristic associated with a patient profile;
identifying, by the monitoring heuristic, physiological movement patterns over time within the sensor signal;
generating, by the monitoring heuristic, an output based on the physiological movement patterns; and
at least one of:
a) generating the patient profile based on an input received by the device configured to include a unique identifier and patient metrics; associating the monitoring heuristic with the patient profile; modifying the monitoring heuristic based on the patient metrics to generate a modified monitoring heuristic; and loading the patient profile including the modified monitoring heuristic; and
b) accessing a patient profile set within a computing system; generating a user interface configured to display the patient profile set; and loading the patient profile that comprises the monitoring heuristic based on an input received via the user interface configured to identify the patient profile from the patient profile set.

18. The computer-readable medium of claim 17, further comprising:
generating the patient profile based on the input received by the device configured to include the unique identifier and patient metrics;
associating the monitoring heuristic with the patient profile;
modifying the monitoring heuristic based on the patient metrics to generate the modified monitoring heuristic; and
loading the patient profile including the modified monitoring heuristic.

19. The computer-readable medium of claim 17, further comprising:
accessing the patient profile set within the computing system;
generating the user interface configured to display the patient profile set;
loading the patient profile that comprises the monitoring heuristic based on the input received via the user interface configured to identify the patient profile from the patient profile set.

20. The computer-readable medium of claim 17, further comprising:
generating the sensor signal in relation to a detected pressure distribution imposed on a sensor array, wherein the physiological movement is a change in the detected pressure distribution over time.

21. The computer-readable medium of claim 17, further comprising:
modifying the monitoring heuristic according to the physiological movement patterns to detect discrete variations in the sensor signal.

22. The computer-readable medium of claim 17, further comprising:
determining a status of the patient is stable when the output indicates that the physiological movement is greater than or equal to a minimal change threshold, and
determining the status of the patient is alert when the output indicates that the physiological movement is less than a minimal change threshold and that a counter matches or exceeds a threshold time value.

23. The computer-readable medium of claim 17, further comprising:
controlling an administration rate of medications based on the output.

24. The computer-readable medium of claim 17, further comprising:
generating reports based on the output; and
transmitting reports to a monitoring system configured to respond with patient care instructions.

* * * * *